(12) United States Patent
Daifuku et al.

(10) Patent No.: US 9,493,500 B2
(45) Date of Patent: Nov. 15, 2016

(54) FLUORINATED PYRIMIDINE ANALOGS AND METHODS OF USE THEREOF

(71) Applicant: Richard Daifuku, Mercer Island, WA (US)

(72) Inventors: Richard Daifuku, Mercer Island, WA (US); Anna Gall, Woodinville, WA (US); Dmitri S. Sergueev, Bothell, WA (US)

(73) Assignee: Richard Daifuku, Mercer Island, WA (US)

( * ) Notice: Subject to any disclaimer, the term of this patent is extended or adjusted under 35 U.S.C. 154(b) by 272 days.

(21) Appl. No.: 13/843,439

(22) Filed: Mar. 15, 2013

(65) Prior Publication Data

US 2014/0024612 A1 Jan. 23, 2014

Related U.S. Application Data

(60) Provisional application No. 61/673,554, filed on Jul. 19, 2012.

(51) Int. Cl.
| | | |
|---|---|---|
| *C07H 19/06* | (2006.01) | |
| *C07H 19/12* | (2006.01) | |
| *A01N 43/04* | (2006.01) | |
| *A61K 31/70* | (2006.01) | |

(52) U.S. Cl.
CPC .............. *C07H 19/12* (2013.01); *C07H 19/06* (2013.01)

(58) Field of Classification Search
CPC ................................ C07H 19/12; C07H 19/06
See application file for complete search history.

(56) References Cited

U.S. PATENT DOCUMENTS

| | | | | |
|---|---|---|---|---|
| 5,371,210 A | * | 12/1994 | Chou | C07H 19/04 536/27.11 |
| 5,401,838 A | * | 3/1995 | Chou | C07H 19/04 536/28.1 |
| 6,548,486 B1 | | 4/2003 | Dalen | |
| 6,933,287 B1 | | 8/2005 | Greer | |
| 7,250,416 B2 | * | 7/2007 | Phiasivongsa | C07D 251/16 514/241 |
| 8,158,605 B2 | | 4/2012 | Silverman | |
| 8,399,420 B2 | | 3/2013 | Silverman | |
| 2006/0128653 A1 | | 6/2006 | Tang | |
| 2006/0128654 A1 | | 6/2006 | Tang | |
| 2008/0057086 A1 | * | 3/2008 | Etter | A61K 9/2846 424/400 |
| 2010/0311683 A1 | * | 12/2010 | Beach | A61K 31/7068 514/49 |
| 2011/0042247 A1 | | 2/2011 | Kocherlakota | |
| 2013/0001818 A1 | | 1/2013 | Fujioka | |

FOREIGN PATENT DOCUMENTS

WO 2012/106299 A1 8/2012

OTHER PUBLICATIONS

International Search Report and Written Opinion mailed Dec. 23, 2013, issued in corresponding International Application No. PCT/US2013/032593, filed Mar. 15, 2013, 11 pages.

* cited by examiner

*Primary Examiner* — Lawrence E Crane
(74) *Attorney, Agent, or Firm* — Christensen O'Connor Johnson Kindness PLLC

(57) ABSTRACT

The present invention provides fluorinated 5-aza-2'-deoxycytidine compounds, such as 2',2'-difluoro-5-aza-2'-deoxycytidine, compositions that include the compounds, methods for making the compounds, and methods for inhibiting DNA methyltransferase, treating solid tumors, and treating hematologic cancers by administering the compounds.

22 Claims, 7 Drawing Sheets

FLUORINATED PYRIMIDINE ANALOGS AND METHODS OF USE THEREOF

CROSS-REFERENCE TO RELATED APPLICATION

This application claims the benefit of U.S. Provisional Application No. 61/673,554, filed Jul. 19, 2012, expressly incorporated herein by reference in its entirety.

BACKGROUND OF THE INVENTION

Figure 1:
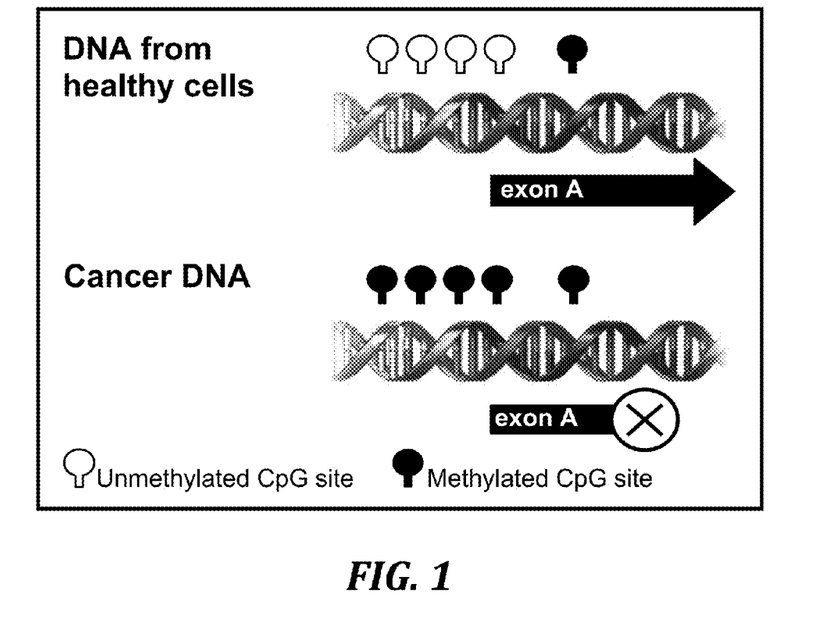
FIG. 1 is a schematic illustration of overexpression of DNA methyl transferase (DNMT), as occurs in cancer cells, can lead to hypermethylation and inactivation of promoters of tumor suppression and growth regulatory genes.

Aberrant DNA methylation is an epigenetic mechanism that can inactivate the expression of genes that suppress tumorigenesis. The genes involved include tumor suppressor genes; genes that suppress apoptosis, metastasis and angiogenesis; genes that repair DNA; and genes that express tumor-associated antigens. The molecular mechanism of silencing gene expression appears to be due to the attachment of 5-methylcytosine binding proteins to the methylated promoter, which blocks the action of transcription factors (see FIG. 1).

Figure 2:
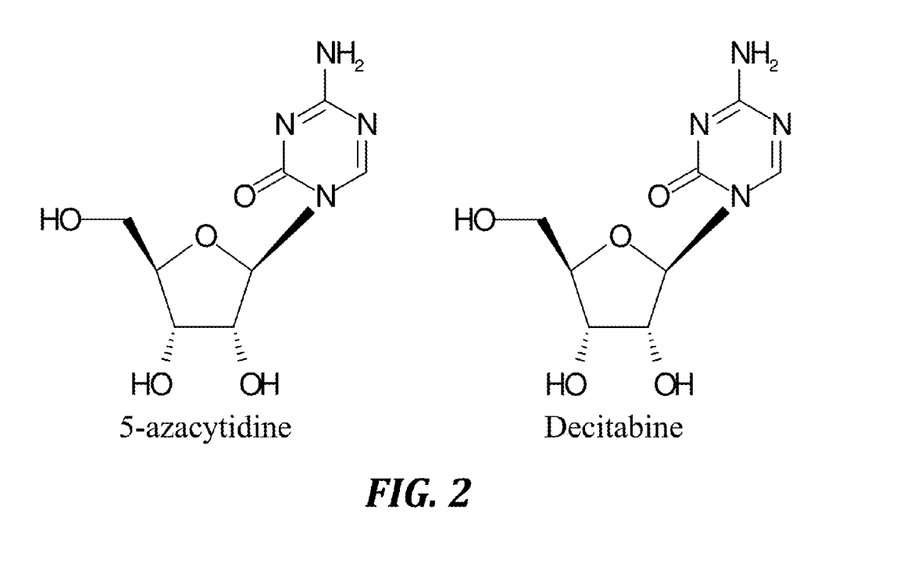
FIG. 2 illustrates the chemical structures of 5-azacytidine and decitabine.

Because this epigenetic change is reversible, it presents an interesting target for chemotherapeutic intervention. 5-Azacytidine was the first hypomethylating agent approved by the FDA for the treatment of a neoplasm and the deoxyanalog, 5-azadeoxycytidine or decitabine, was more recently approved for the same indication (see FIG. 2). Both drugs produce remissions or clinical improvements in more than half of the treated patients with myelodysplatic syndrome (MDS). Features of responses include the requirement for multiple cycles of therapy, slow responses, and actual clonal elimination. Optimization of therapy has included (1) reducing the dose to favor hypomethylation over cytotoxicity, (2) prolonging administration schedules, and (3) increasing dose intensity without reaching cytotoxicity. Molecularly, hypomethylation and gene reactivation have been shown and seem to be required for responses. The data in MDS represent a proof-of-principle for epigenetic therapy. Although the therapy is effective, with complete responses lasting months to years in some patients, resistance seems to develop in the majority of patients, and the mechanisms of resistance are unknown.

Data from the two currently approved drugs suggest that myeloid malignancies are the neoplasms most sensitive to inhibitors of DNA methylation. However, there is no known reason why solid tumors should not respond as well. Recently, preclinical studies with DNA methyl transferase inhibitors (DNMTIs) have demonstrated that they are also potent angiostatic agents, inhibiting tumor endothelial cells and angiogenesis in vitro and in vivo, adding to the rationale for the treatment of solid tumors with these agents.

Figure 3:
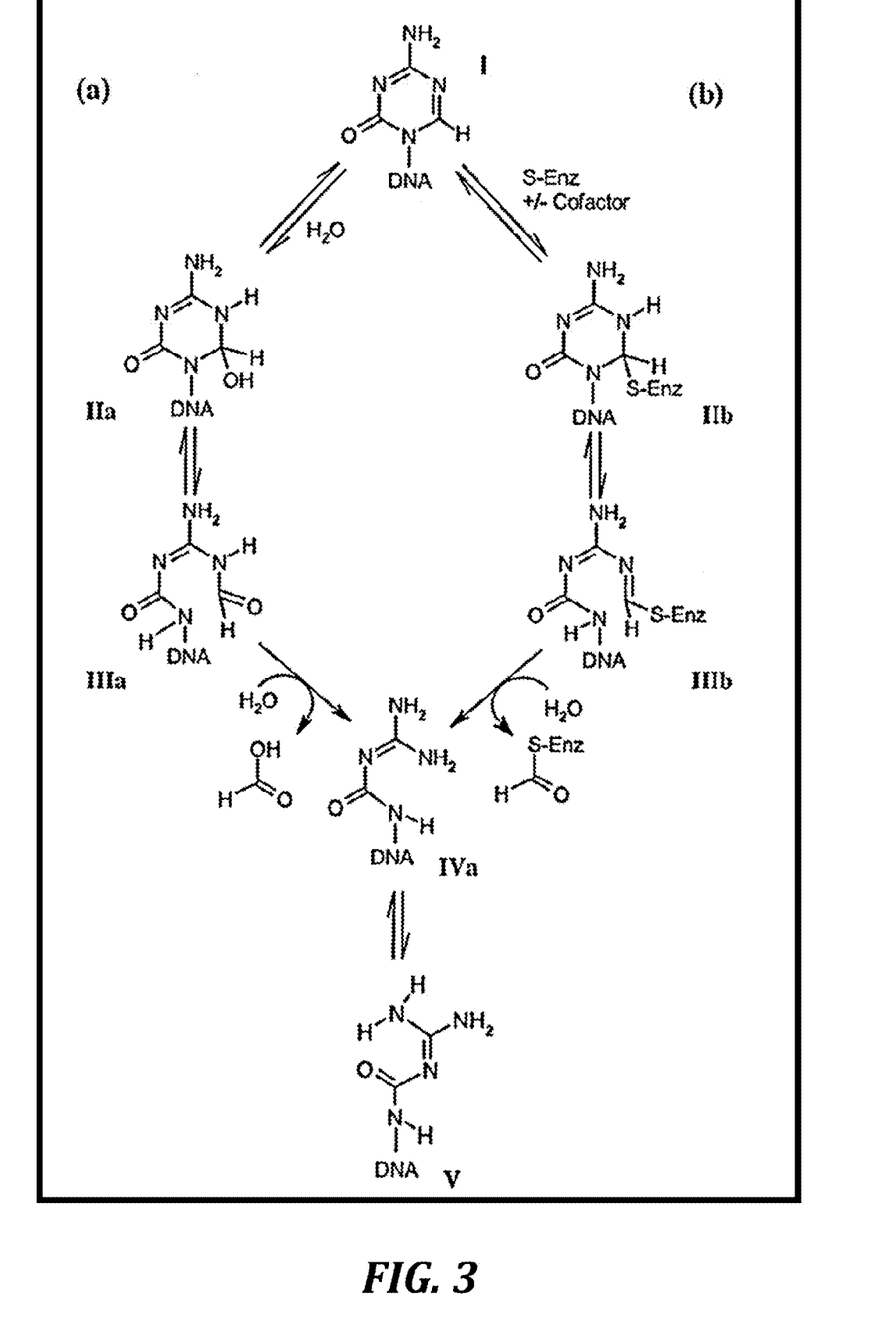
FIG. 3 illustrates reaction pathways for ring opening and hydrolysis of 5-azacytosine residue in DNA in solution (a) and after covalent linkage to the active site of a DNMT (b).

5-Azacytidine and decitabine are known to be unstable in water, with cleavage of the base at the 6-position of the cytosine ring (see FIG. 3, IIIa). Both nucleosides are known to suffer from a short half-life. The half-life of 5-azacytidine following subcutaneous administration is reported to be 41 minutes and that of decitabine 30 minutes. Both drugs are good substrates for cytidine deaminase and the short half-life is primarily due to deamination of the base to inactive uracil.

Figure 4:
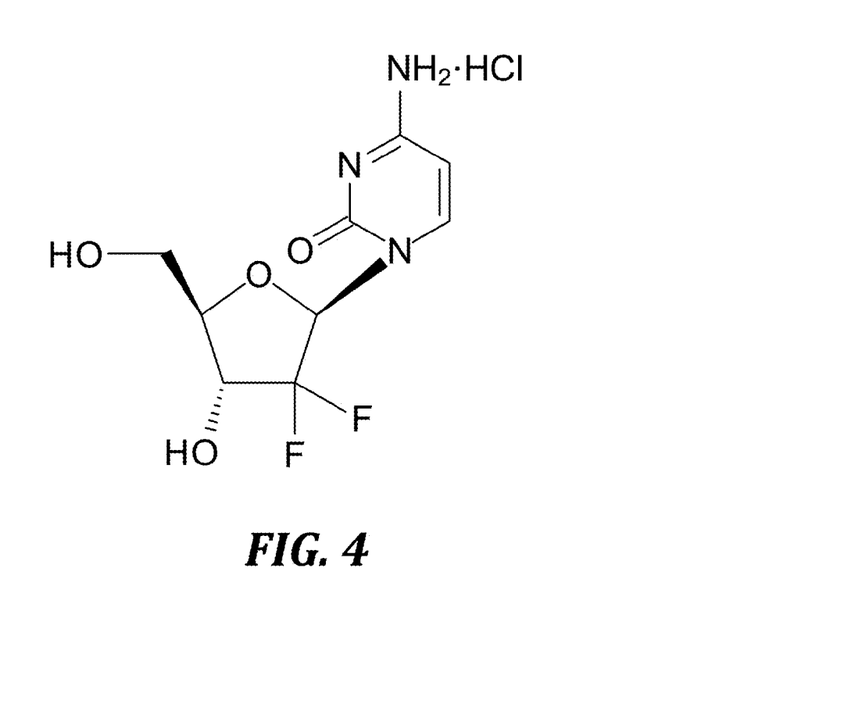
FIG. 4 illustrates the chemical structure of gemcitabine HCl.

Gemcitabine differs from cytidine by a difluorinated sugar at the 2'-position. See FIG. 4.

The cytotoxic effect of gemcitabine is attributed to a combination of two actions of the diphosphate and the triphosphate nucleosides, which leads to inhibition of DNA synthesis. First, gemcitabine diphosphate inhibits ribonucleotide reductase, which is responsible for catalyzing the reactions that generate the deoxynucleoside triphosphates for DNA synthesis. Inhibition of this enzyme by the diphosphate nucleoside causes a reduction in the concentrations of deoxynucleotides, including dCTP. Second, gemcitabine triphosphate competes with dCTP for incorporation into DNA. The reduction in the intracellular concentration of dCTP (by the action of the diphosphate) enhances the incorporation of gemcitabine triphosphate into DNA (self-potentiation). After the gemcitabine nucleotide is incorporated into DNA, only one additional nucleotide is added to the growing DNA strands. After this addition, there is inhibition of further DNA synthesis. DNA polymerase epsilon is unable to remove the gemcitabine nucleotide and repair the growing DNA strands (masked chain termination).

There exists a need for novel cancer therapeutics with improved efficacy, safety, and/or pharmacokinetic profiles. The invention provides novel fluorinated pyrimidine analogs and compositions for the treatment of cancer.

SUMMARY OF THE INVENTION

In one aspect, the invention provides fluorinated pyrimidine analogs.

In one embodiment, the invention provides 2',2'-difluoro-5-azadeoxycytidine, its anomers, and pharmaceutically acceptable salts thereof.

In another embodiment, the invention provides 2',2'-difluoro-5,6-dihydro-5-azadeoxycytidine, its anomers, and pharmaceutically acceptable salts thereof.

In a further embodiment, the invention provides 2'-deoxy-2',2'-difluorozebularine, its anomers, and pharmaceutically acceptable salts thereof.

In another aspect, the invention provides pharmaceutical compositions that include the fluorinated pyrimidine analogs. The pharmaceutical compositions include one or more of the fluorinated pyrimidine analogs, a pharmaceutically acceptable carrier or diluent, and optionally, one or more additional therapeutic agents. The pharmaceutical compositions are useful for the administration of fluorinated pyrimidine analogs to treat cancer.

In other aspects of the invention, methods for inhibiting DNA methyltransferase and methods for treating cancers using the fluorinated pyrimidine analogs are provided.

In one aspect, the invention provides a method for inhibiting DNA methyltransferase in a subject, comprising administering to the subject a therapeutically effective amount of 2',2'-difluoro-5-azadeoxycytidine, its anomers, and pharmaceutically acceptable salts thereof.

In another aspect, the invention provides a method for treating a cancer treatable by inhibiting DNA methyltransferase, comprising administering to a subject in need thereof a therapeutically effective amount of 2',2'-difluoro-5-azadeoxycytidine, its anomers, and pharmaceutically acceptable salts thereof.

In a further aspect, the invention provides a method of treating a solid tumor carcinoma, comprising administering to a subject in need thereof a therapeutically effective amount of 2',2'-difluoro-5-azadeoxycytidine, its anomers, and pharmaceutically acceptable salts thereof. In certain embodiments, the solid tumor carcinoma is selected from breast, non-small cell lung, colon, renal, ovarian, and colorectal carcinomas.

In another embodiment, the invention provides a method of treating a hematologic malignancy, comprising administering to a subject in need thereof a therapeutically effective amount of 2',2'-difluoro-5-azadeoxycytidine, its anomers, and pharmaceutically acceptable salts thereof. In certain embodiments, the hematologic malignancy is a leukemia. In certain embodiments, the leukemia is resistant to decitabine (5-azadeoxycytidine).

In one aspect, the invention provides a method of treating a solid tumor carcinoma, comprising administering to a subject in need thereof a therapeutically effective amount of 2',2'-difluoro-5,6-dihydro-5-azadeoxycytidine, its anomers, and pharmaceutically acceptable salts thereof. In certain embodiments, the solid tumor carcinoma is selected from breast, non-small cell lung, and colon carcinomas.

In another embodiment, the invention provides a method of treating a hematologic malignancy, comprising administering to a subject in need thereof a therapeutically effective amount of 2',2'-difluoro-5,6-dihydro-5-azadeoxycytidine, its anomers, and pharmaceutically acceptable salts thereof. In certain embodiments, the hematologic malignancy is a leukemia.

In a further aspect, the invention provides a method of treating a solid tumor carcinoma, comprising administering to a subject in need thereof a therapeutically effective amount of 2'-deoxy-2',2'-difluorozebularine, its anomers, and pharmaceutically acceptable salts thereof. In certain embodiments, the solid tumor carcinoma is selected from breast, non-small cell lung, colon, and colorectal carcinomas.

In another embodiment, the invention provides a method of treating a hematologic malignancy, comprising administering to a subject in need thereof a therapeutically effective amount of 2'-deoxy-2',2'-difluorozebularine, its anomers, and pharmaceutically acceptable salts thereof. In certain embodiments, the hematologic malignancy is a leukemia.

In any of the methods noted above, the subject can be a human subject.

In other aspects, the invention provides methods for making the fluorinated pyrimidine analogs.

DETAILED DESCRIPTION OF THE INVENTION

The present invention provides therapeutic drug compounds that are useful in the treatment of cancer. The therapeutic drug compounds of the invention are fluorinated pyrimidine analogs. The present invention also provides compositions that include the fluorinated pyrimidine analogs, methods for making the fluorinated pyrimidine analogs, and methods for treating cancer using the fluorinated pyrimidine analogs.

The therapeutic drug compounds are a family of DNA methyl transferase inhibitors (DNMTIs) that substitute the sugar moiety from gemcitabine for the natural sugar.

In one aspect, the present invention provides fluorinated pyrimidine analogs. Representative fluorinated pyrimidine analogs of the invention include:

2',2'-difluoro-5-azadeoxycytidine (referred to herein as "NUC013");

2',2'-difluoro-5,6-dihydro-5-azadeoxycytidine (referred to herein as "NUC014"); and 2'-deoxy-2',2'-difluorozebularine (referred to herein as "NUC019").

In one embodiment, the invention provides 2',2'-difluoro-5-azadeoxycytidine, its anomers (α and β), and salts thereof.

In another embodiment, the invention provides 2',2'-difluoro-5,6-dihydro-5-azadeoxycytidine, its anomers (α and β), and salts thereof.

In a further embodiment, the invention provides 2'-deoxy-2',2'-difluorozebularine, its anomers (α and β), and salts thereof.

Suitable salts include pharmaceutically acceptable salts. Representative salts include acetate, adipate, aspartate, benzoate, benzene sulfonate (besylate), bisulfate, butyrate, citrate, camphorate, camphorsulfonate, cyclopentane propionate, digluconate, dodecylsulfate, 1,2-ethane disulfonate (edisylate), ethane sulfonate (esylate), formate, fumarate, glucoheptanoate, glycerophosphate, glycolate, hemisulfate, heptanoate, hexanoate, hydrochloride, hydrobromide, hydroiodide, 2-hydroxyethane sulfonate, lactate, maleate, methane sulfonate (mesylate), 2-naphthalene sulfonate (napsylate), nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate, and undecanoate salts.

In another aspect, the present invention provides pharmaceutical compositions comprising at least one fluorinated pyrimidine analog of the invention together with a pharmaceutically acceptable carrier or diluent suitable for administration to a human or animal subject, either alone or together with other therapeutics and/or anticancer agents. The fluorinated pyrimidine analogs of the invention may be formulated into a composition that additionally comprises suitable pharmaceutically acceptable carriers, including excipients and other compounds that facilitate administration of the fluorinated pyrimidine analogs to a mammalian subject. The pharmaceutical compositions are useful for the administration of fluorinated pyrimidine analogs to treat cancer.

Compositions that include one or more fluorinated pyrimidine analogs of the invention are administered to deliver therapeutically effective amounts of the fluorinated pyrimidine analog. Therapeutically effective amounts of the fluorinated pyrimidine analog(s) will generally range up to the maximally tolerated dosage, but the concentrations are not critical and may vary widely. The precise amounts employed by the attending physician will vary, of course, depending on the compound, route of administration, physical condition of the patient and other factors. The daily dosage may be administered as a single dosage or may be divided into multiple doses for administration. Administration of the fluorinated pyrimidine analogs of the invention is accomplished by any effective route, for example, parenterally or orally.

The amount of the fluorinated pyrimidine analogs of the invention actually administered will be a therapeutically effective amount, which term is used herein to denote the amount needed to produce a substantial beneficial effect. Effective doses may be extrapolated from dose-response curves derived from in vitro or animal model test systems. The animal model is also typically used to determine a desirable dosage range and route of administration. Such information can then be used to determine useful doses and routes for administration in humans or other mammals. The determination of an effective dose is well within the capability of those skilled in the art. Thus, the amount actually administered will be dependent upon the individual to which treatment is to be applied, and will preferably be an optimized amount such that the desired effect is achieved without significant side-effects.

In another aspect of the invention, methods for making the fluorinated pyrimidine analogs are provided. The preparation of 2',2'-difluoro-5-azadeoxycytidine (NUC013) is provided in EXAMPLE 1. The preparation of 2',2'-difluoro-5,6-dihydro-5-azadeoxycytidine (NUC014) is provided in EXAMPLE 2. The preparation of 2',2'-difluorozebularine (NUC019) is provided in EXAMPLE 3.

In another aspect, the present invention provides methods of treating human or animal subjects suffering from a cellular proliferative disease, such as cancer, using the fluorinated compounds of the invention. Representative cell proliferative diseases treatable by the compounds of the invention include hematologic cancers, such as leukemia, lymphoma, and myeloma, and nonhematologic cancers, such as solid tumor carcinomas (e.g., breast, ovarian, pancreatic, colon, colorectal, non-small lung, renal, and bladder), sarcomas, and gliomas. The present invention provides methods of treating a human or animal subject in need of such treatment, comprising administering to the subject a therapeutically effective amount of one or more fluorinated pyrimidine analogs of the invention, either alone or in combination with one or more other therapeutic and/or anticancer agents.

Representative Fluorinated Pyrimidine Compounds

The primary rationale for the development of this family of molecules is based on the mechanism of self-potentiation noted with gemcitabine, though such molecules may present other interesting characteristics.

NUC013. 2',2'-difluoro-5-azadeoxycytidine (NUC013) (see FIG. 5) is a novel cytidine analog, related to 5-azacytidine and decitabine, hence producing known metabolites. Having known metabolites facilitates clinical development by decreasing the risk of unforeseen toxicities. For example, metabolite toxicity has complicated the clinical development of 5-fluorodeoxycytidine as a DNMTI.

NUC013 has been screened for activity in cell lines and compared to 5-azacytidine and decitabine. See Table 1.

TABLE 1

In vitro cytotoxicity of NUC013 compared to decitabine and 5-azacytidine.

| Compound | Breast MDA-MB-231 (µM) | NSCL NCI-H460 (µM) | Colon HCT-116 (µM) | Leukemia L1210 (µM) | Renal ACHN* (µM) | Ovarian OVCAR-8* (µM) | Leukemia P388* (µM) |
|---|---|---|---|---|---|---|---|
| Decitabine | >62.5 | 13-44 | >62.5 | 0.24 | >1000 | >1000 | 0.0004 |
| Azacytidine | 1.64 | 0.43 | 0.62 | 1.7-2.4 | 2.51 | 6.38 | 0.74 |
| NUC013 | >62.5 | 4.39 | 4.54 | 1.02 | 0.89 | 25.88 | 0.48 |

As can be seen from Table 1, the cytotoxicity of NUC013 against various tumor cells lines, both solid and hematologic, has a unique profile. NUC013 is active against cell lines that are resistant to decitabine, particularly solid tumor cell lines.

Figure 6:
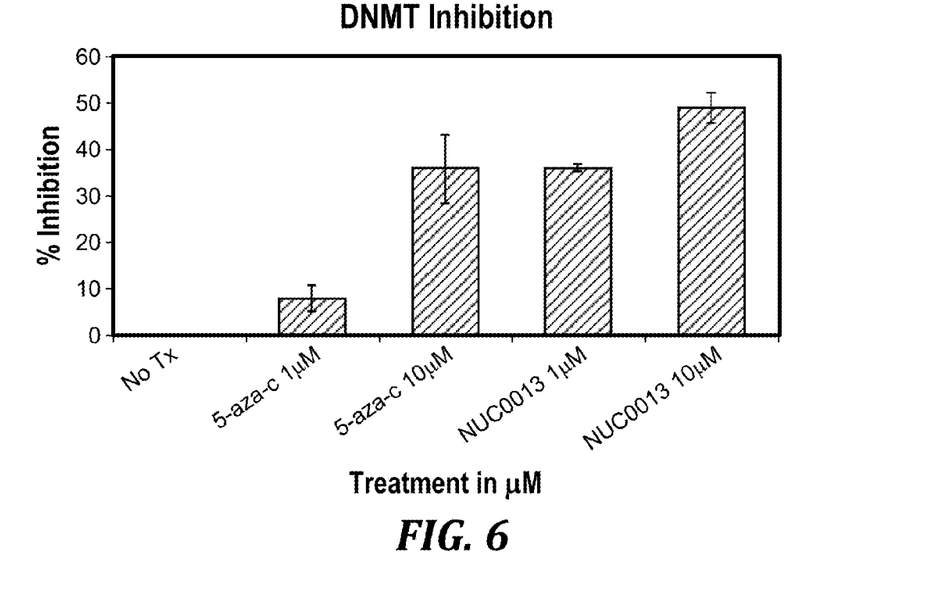
FIG. 6 compares DNMT inhibition in colon cancer cells (HCT116) of NUC013 and 5-azacytidine.

NUC013 has also been tested for DNA methyl transferase inhibition (see FIG. 6). In colon cancer cells, NUC013 is approximately 10-fold more potent than 5-azacytidine as a DNMTI. However, as 5-azacytidine is more cytotoxic than NUC013 in this cell line ($GI_{50}$ of 0.62 µM versus 4.54 µM, respectively), it is possible to achieve substantial inhibition of DNMT at drug concentrations that are less cytotoxic with NUC013 compared to 5-azacytidine.

Figure 7:
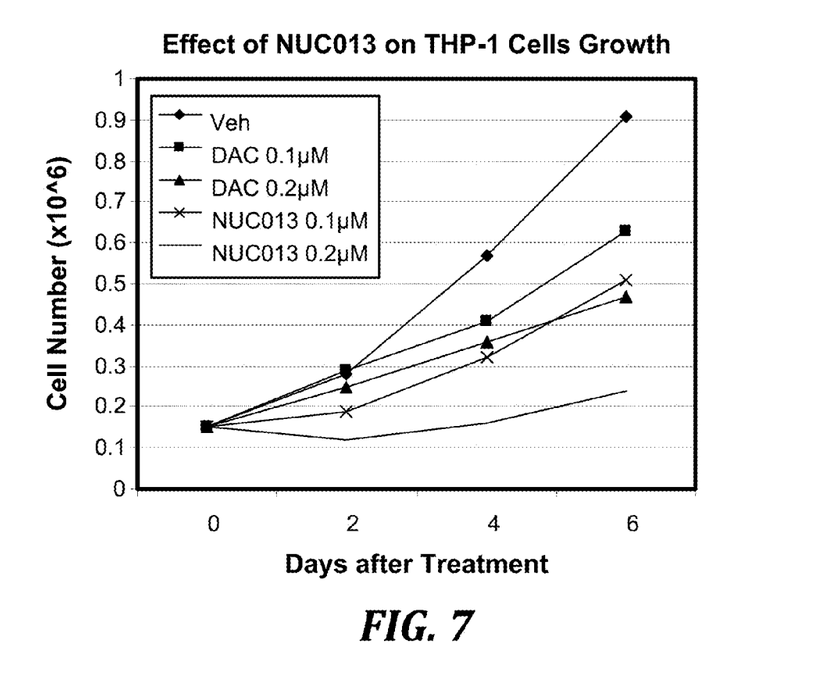
FIG. 7 compares the activity of NUC013 and decitabine (DAC) on the THP-1 leukemia cell line.
Figure 8:
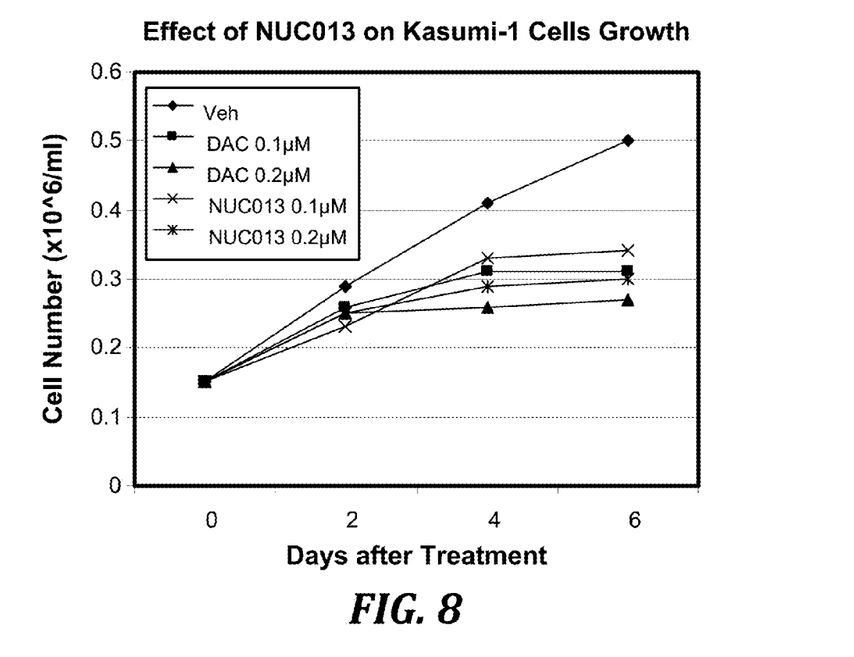
FIG. 8 compares the activity of NUC013 and decitabine (DAC) on the Kasumi-1 leukemia cell line.
Figure 9:
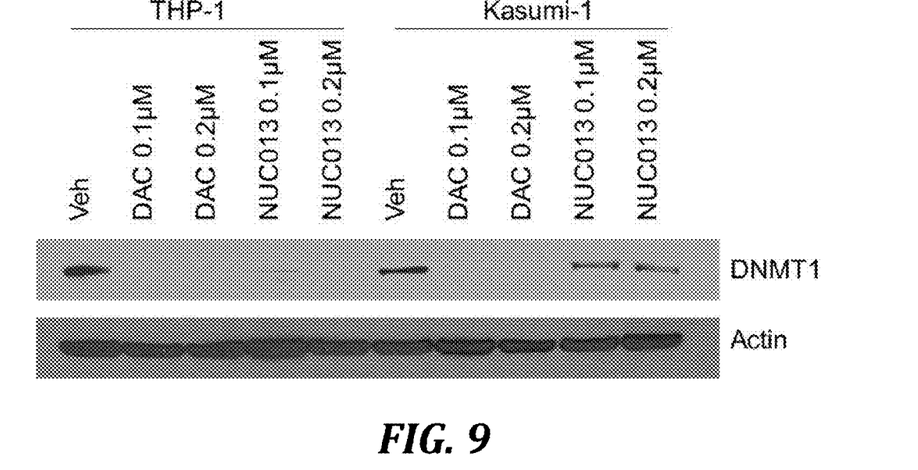
FIG. 9 illustrates Western blot comparing inhibitory activity against DNMT1 of decitabine and NUC013 in THP-1 and Kasumi-1 cell lines.

FIG. 7 compares the activity of NUC013 with that of decitabine on leukemia cell lines THP-1 and Kasumi 1. FIG. 8 compares the activity of NUC013 and decitabine (DAC) on the Kasumi-1 leukemia cell line. NUC013 displayed a stronger inhibitory effect on THP-1 leukemia cells growth than decitabine, but a slightly weaker effect in Kasumi-1 cells at equimolar concentrations. FIG. 9 illustrates Western blot comparing inhibitory activity against DNMT1 of decitabine and NUC013 in THP-1 and Kasumi-1 cell lines.

Figure 5:
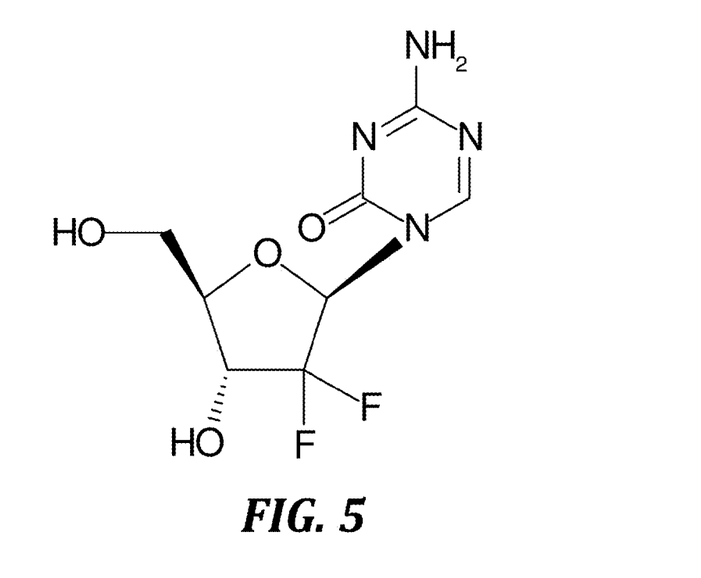
FIG. 5 illustrates the chemical structure of 2',2'-difluoro-5-azadeoxycytidine (NUC013).

In comparisons with decitabine, depletion of DNMT1 by NUC013 appears to be related to the cytoreduction demonstrated in FIGS. 5 and 6. Indeed, at the two concentrations tested in FIG. 7, NUC013 demonstrates similar DNMT inhibition by Western blot compared with equimolar decitabine in THP-1 cells, while demonstrating stronger cytoreduction, but has weaker DNMT1 inhibition on Kasumi-1 cells correlating with weaker cytoreduction. These data further confirm that NUC013 is a DNMT inhibitor.

Figure 10:
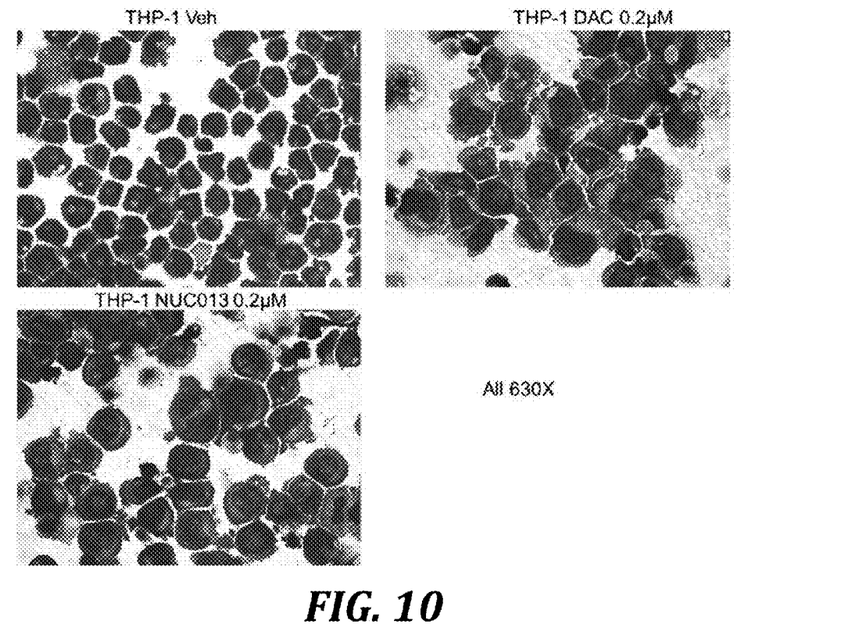
FIG. 10 compares Giemsa stain of THP-1 cells treated with decitabine or NUC013 compared to vehicle control.
Figure 11:
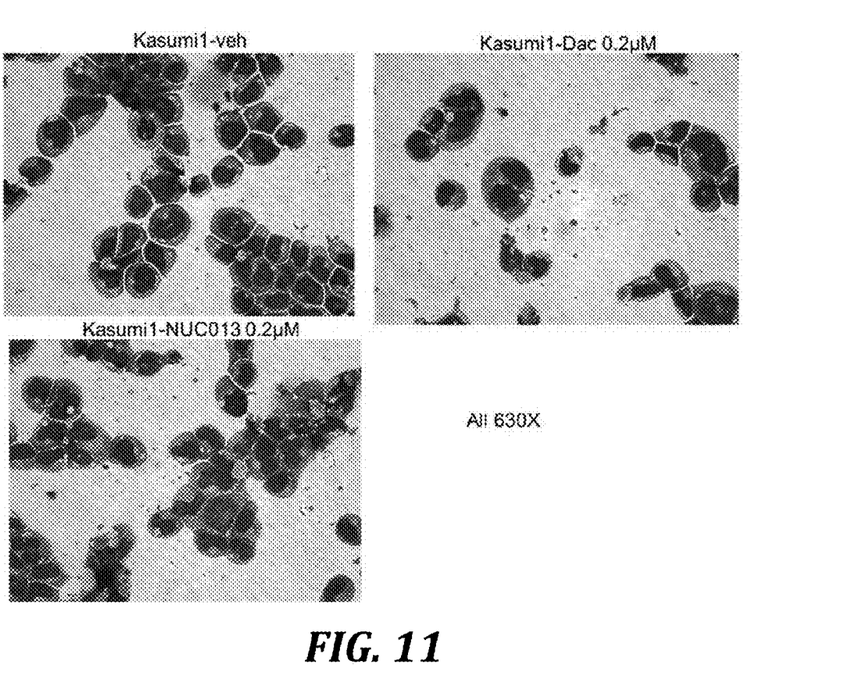
FIG. 11 compares Giemsa stain of Kasumi-1 cells treated with decitabine or NUC013 compared with vehicle control.

FIG. 10 compares Giemsa stain of THP-1 cells treated with decitabine or NUC013 compared to vehicle control. FIG. 11 compares Giemsa stain of Kasumi-1 cells treated with decitabine or NUC013 compared with vehicle control.

As demonstrated in FIGS. 8 and 9, treatment of THP-1 or Kasumi-1 cells by NUC013 or decitabine results in morphologic changes suggestive of cell differentiation, with greater effects observed for NUC013 treatment of THP-1 than Kasumi-1 cells, compatible with greater DNMT1 inhibition in THP-1 cells.

The preparation of 2',2'-difluoro-5-azadeoxycytidine (NUC013) is described in Example 1. In vitro cytotoxicity of NUC013 (non-small cell lung, colorectal, leukemia, and breast cancer) is described in Example 4. In vitro DNA methyltransferase inhibition of NUC013 is described in Example 5.

Figure 12:
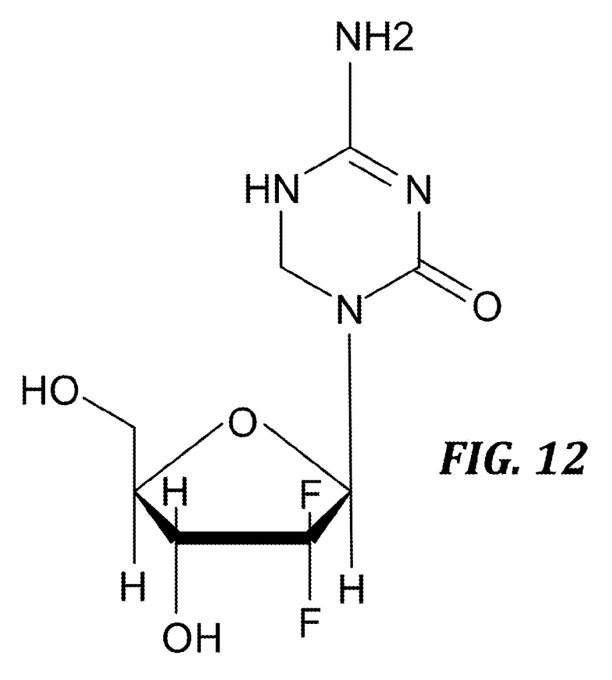
FIG. 12 illustrates the chemical structure of 2',2'-difluoro-5,6-dihydro-5-azadeoxycytidine (NUC014).

NUC014. NUC014 is the 5,6-dihydro derivative of NUC013. FIG. 12 illustrates the chemical structure of 2',2'-difluoro-5,6-dihydro-5-azadeoxycytidine (NUC014). It has been found to be stable in an aqueous environment and does not undergo hydrolytic cleavage at the 6-position of the cytosine. Representative in vitro cytotoxicity of NUC014 is summarized in Table 2.

TABLE 2

In vitro cytotoxicity of NUC014.

| Compound | Breast MDA-MB-231 ($\mu$M) | NSCL NCI-H460 ($\mu$M) | Colon HCT-116 ($\mu$M) | Leukemia L1210 ($\mu$M) |
| --- | --- | --- | --- | --- |
| NUC014 | >31.25 | >31.25 | >31.25 | 90.58 |

NUC014 demonstrates moderate cytotoxicity against leukemia cell line L1210. Based on available data showing lesser cytotoxicity for 5,6-dihydro-5-aza-2'-deoxycytidine (DHADC) compared to decitabine, it is not surprising that NUC014 is also less cytotoxic than NUC013.

The preparation of 2',2'-difluoro-5,6-dihydro-5-azadeoxycytidine (NUC014) is described in Example 2.

Figure 13:
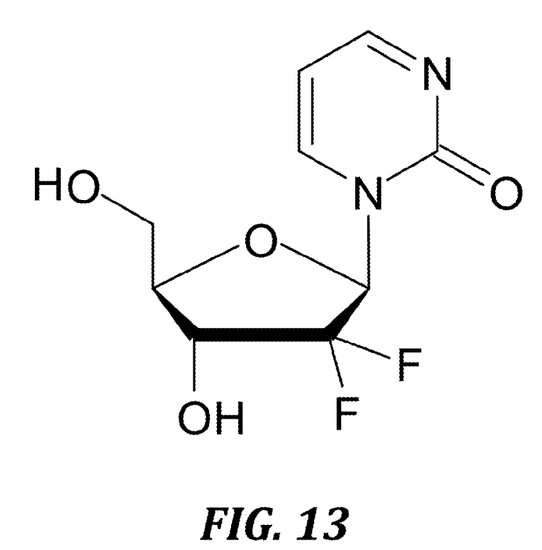
FIG. 13 illustrates the chemical structure of 2'-deoxy-2', 2'-difluorozebularine (NUC019).

NUC019 and NUC020. NUC019 is a derivative of zebularine. FIG. 13 illustrates the chemical structure of 2'-deoxy-2',2'-difluorozebularine (NUC019). Representative in vitro cytotoxicity of zebularine and zebularine derivatives NUC019 and its α-anomer NUC020 is summarized in Table 3.

TABLE 3

In vitro cytotoxicity of zebularine and zebularine derivatives

| Compound | Breast MDA-MB-231 ($\mu$M) | NSCL NCI-H460 ($\mu$M) | Colon HCT-116 ($\mu$M) | Leukemia L1210 ($\mu$M) |
| --- | --- | --- | --- | --- |
| Zebularine | 143.92 | 99.08 | 47.88 | 108.27 |
| NUC019 | 165.90 | 135.65 | 310.26 | 320.95 |
| NUC020 | 212.92 | 135.94 | 278.69 | 346.21 |

The preparation of 2'-deoxy-2',2'-difluorozebularine (NUC019) is described in Example 3. In vitro cytotoxicity of NUC019 (non-small cell lung, colorectal, leukemia, and breast cancer) is described in Example 4.

The following examples are provided for the purpose of illustrating, not limiting, the invention.

EXAMPLE 1

Preparation of 2',2'-Difluoro-5-azadeoxycytidine (NUC013)

Two alternative pathways, shown in Scheme I, were used to prepare 2',2'-difluoro-5-azadeoxycytidine (Compound IV) (NUC013).

A. Preparation of 3',5'-dibenzoyl-2',2'-difluoro-5-azadeoxycytidine (Compound III) via 1-bromo-2-deoxy-2,2-difluoro-D-ribofuranosyl-3,5-dibenzoate (Compound I).

(1) The starting material 2-deoxy-2,2-difluoro-D-ribofuranosyl-3,5-dibenzoate known in the art (Chou, et. al., Synthesis 1992, v.p. 565-570) was converted to 1-bromo analog by a method similar to the one described in International Patent Application WO 2006/070985. The starting ribose (3.9 g, 10.3 mmol) was dissolved in 31 ml of toluene and dry triethylamine (1.43 ml, 10.3 mmol) was added. The solution was cooled to 0° C. and diphenyl phosphoryl chloride (2.64 ml, 12.3 mmol) in 8 ml of toluene was added during 15 min. The reaction mixture was warmed up to room temperature and incubated for 3.5 hours. The reaction was quenched by addition of 1 M HCl (10.2 ml), the toluene layer was separated and aqueous layer was extracted back with 10 ml ether. The organic layers were combined, extracted consequently with water, saturated NaHCO$_3$, and saturated NaCl (each 20 ml) and dried over MgSO$_4$. The solvents were removed and the product was isolated by flash chromatography on silica gel in hexane-ethyl acetate gradient. Yield 4.6 g, 73%.

(2) To the intermediate diphenylphosphate analog (4.6 g, 7.5 mmol) prepared as described in Step (1), was added HBr in acetic acid (30%, 16.2 ml, 81.3 mmol) and the reaction mixture was incubated for 6.5 h at room temperature. The reaction mixture was diluted with 80 ml of methylene chloride and extracted twice with ice water, saturated NaHCO$_3$, and saturated NaCl (each 100 ml). The organic layer was dried with MgSO$_4$, filtered and evaporated to yield 1-bromo-2-deoxy-2,2-difluoro-D-ribofuranosyl-3,5-dibenzoate (Compound I, 3.1 g, 93%), which is a 9:1 mixture of α and β isomers.

(3) 5-Azacytosine (98%, Aldrich, 5.0 g, 44.8 mmol) and ammonium sulfate (25 mg) were suspended in hexamethyldisilazane (25 ml) and chlorotrimethylsilane (0.2 ml) was added. The reaction mixture was heated at the reflux for 17 h. The clear solution was cooled, evaporated, coevaporated twice with dry xylene and vacuum dried to yield whitish solids of the silylated 5-azacytosine (~7 g) which is used in whole for the next glycosylation step.

(4) For glycosylation step 1-bromo-2-deoxy-2,2-difluoro-D-ribofuranosyl-3,5-dibenzoate (Compound I) (0.78 g, 1.77 mmol), prepared as described in Step (2), was dissolved in 4 ml anisole and transferred to the silylated 5-azacytosine solids prepared as in Step (3). The suspension was heated to 150° C. and 2 ml of anisole was added to complete dissolution of all solids. After 4 hours the reaction mixture was cooled and SnCl$_4$ (0.2 ml, 2 mmol) was added. The reaction mixture was reheated to 150° C. for 6 hours, cooled to room temperature, quenched by addition of methylene chloride (30 ml), methanol (10 ml) and silica gel (20 g) and dried to yield 3',5'-dibenzoyl-2',2'-difluoro-5-azadeoxycytidine (Compound III). The resulting powder was applied on the top of the packed silica gel column and products were isolated by flash chromatography in chloroform-methanol gradient. β-Isomer was eluted first followed by α-isomer (only partial separation was achieved, yield for β-isomer 12%, α-isomer 5%). Complete isomer separation was achieved by RP HPLC on Gemini C18 5u (21.2×250 mm column) in 50 mM triethylammonium acetate (pH 7.5)-acetonitrile gradient.

$^1$H NMR in CDCl$_3$ for compound III β-isomer: 8.12 ppm (s, 1H, H6), 7.8-8.1 (m, 4H, benzoyl), 7.4-7.6 (m, 2H, benzoyl), 7.2-7.4 (m, 4H, benzoyl), 6.38 (br.t, J=8.0 Hz, 1H, H1'), 5.65 (m, 1H, H3'), 4.70 (m, 2H, H5'), 4.58 (m, 1H, H4'). ESI MS: 473.3 [M+H]$^+$, 471.1 [M−H]$^−$.

B. Preparation of 2',2'-difluoro-5-azadeoxycytidine (Compound IV). 3',5'-dibenzoyl-2',2'-difluoro-5-azadeoxycytidine (Compound III) (15 mg, 3:1 mixture of α and β isomers), prepared as in Step A, was dissolved in 2 ml of anhydrous MeOH and 1 M NaOMe in MeOH (0.1 ml) was added. After 1 h at room temperature, the reaction mixture was evaporated and the deprotected isomers were isolated by RP HPLC on Gemini C18 5u (21.2×250 mm column) in 50 mM triethylammonium acetate (pH 7.5)-acetonitrile gradient. Immediately after separation fractions corresponding to β isomer were pooled and evaporated at below 10° C. to yield 0.4 mg (19%) of 2',2'-difluoro-5-azadeoxycytidine (Compound IV).

$^1$H NMR in DMSO-$d_6$ for compound IV β-isomer: 8.48 ppm (s, 1H, H6), 7.79 (br, 2H, NH$_2$), 6.35 (br, 1H, 3'-OH), 6.07 t, J=8.0 Hz, 1H, H1'), 5.30 (br, 1H, 5'-OH), 4.90 (br, 1H, 5'-OH), 4.23 (br. m, 1H, H3'), 3.85 (m, 1H, H4'), 3.78 (m, 1H, H5'), 3.63 (m, 1H, H5'), UV 240 nm (sh) in 50 mM triethylammonium acetate (pH 7.5).

C. Preparation of 3',5'-dibenzoyl-2',2'-difluoro-5-azadeoxycytidine (Compound III) via 1-methylsulfonyl-2-deoxy-2,2-difluoro-D-ribofuranosyl-3,5-dibenzoate (Compound II).

Silylated 5-azacytosine (2.3 g, 9 mmol) prepared as described in Step A(3), was dissolved in 2 ml of anisole at 130° C. 1-Methylsulfonyl-2-deoxy-2,2-difluoro-D-ribofuranosyl-3,5-dibenzoate (Compound II) (0.4 g, 0.87 mmol), prepared as described in the art (Chou, et. al., *Synthesis* v.p. 565-570, 1992), was dissolved in 1 ml of anisole and was added to the hot solution of the silylated 5-azacytosine. The reaction mixture was incubated at 150° C. for 7 hours, cooled to room temperature, quenched by addition of 15 ml methylene chloride, 15 g silica gel and 5 ml methanol and the suspension was dried on vacuum. The resulting powder was applied on the top of the packed silica gel column and products were isolated by flash chromatography in chloroform-methanol gradient. Appropriate fractions were pooled and evaporated to yield 3',5'-dibenzoyl-2',2'-difluoro-5-azadeoxycytidine (Compound III) as 2:1 mixture of α- and β-isomers (100 mg, 25% yield).

D. Preparation of 2',2'-difluoro-5-azadeoxycytidine (Compound IV). 3',5'-dibenzoyl-2',2'-difluoro-5-azadeoxycytidine (Compound III) (80 mg, 2:1 mixture of α and β isomers), prepared as in Step C, was dissolved in 2 ml of anhydrous MeOH and 1 M NaOMe in MeOH (0.1 ml) was added. After 1 h at room temperature, the reaction mixture was evaporated and the deprotected isomers were isolated by RP HPLC on Gemini C18 5u (21.2×250 mm column) in 50 mM triethylammonium acetate (pH 7.5)-acetonitrile gradient. Immediately after separation fractions corresponding to β isomer were pooled, evaporated at below 10° C. to yield 2.1 mg (13%) of 2',2'-difluoro-5-azadeoxycytidine (Compound IV).

RP HPLC retention time and spectral characteristics (i.e. 1H NMR and UV) for Compound IV were the same as in Step B. ESI MS: 265.2 [M+H]$^+$.

Scheme 1. Synthesis of 3',5'-dibenzoyl-2',2'-difluoro-5-azadeoxycytidine (Compound III) and 2',2'-difluoro-5-azadeoxycytidine (Compound IV) (NUC013).

7:3 α:β
II

Ms = methylsulfonyl; TMS = trimethylsilyl; Bz = benzoyl; Ph = phenyl; Me = methyl 25% yield, α:β ratio (3:2)
III

EXAMPLE 2

Preparation of 2',2'-Difluoro-5,6-dihydro-5-azadeoxycytidine (NUC014)

Preparation of 2',2'-difluoro-5,6-dihydro-5-azadeoxycytidine (Compound VI) (NUC014) is shown in Scheme 2.

A. Preparation of 3',5'-dibenzoyl-2',2'-difluoro-5-azadeoxycytidine (Compound V). Pure β-Isomer of 3',5'-dibenzoyl-2',2'-difluoro-5-azadeoxycytidine (Compound III) (144 mg, 0.30 mmol), prepared as in Example 1, was dissolved in 3 ml of methylene chloride and triethylamine (0.12 ml) and chlorotrimethysilane (0.1 ml) were added. After 0.5 hour the reaction mixture was diluted with 5 ml acetic acid and sodium borohydride (100 mg, 2.6 mmol) was added as powder. After 1 h at room temperature the reaction mixture was evaporated and separated by RP HPLC on Gemini C18 5u (21.2×250 mm column) in 50 mM triethylammonium acetate (pH 7.5)-acetonitrile gradient. Fractions corresponding to the product were pooled and evaporated to yield 83 mg (57%) of 3',5'-dibenzoyl-2',2'-difluoro-5-azadeoxycytidine (Compound V).

$^1$H NMR in DMSO-d$_6$ for compound V β-isomer: 7.93-8.07 (m, 4H, benzoyl), 7.64-7.77 (m, 2H, benzoyl), 7.47-7.62 (m, 4H, benzoyl), 6.08 (t, J=7.2 Hz, 1H, H1'), 5.63 (m, 1H, H3'), 4.55-4.70 (m, 3H, H4' and H5'), 4.48 (s, 2H, CH$_2$). ESI MS: 475.4 [M+H]$^+$.

B. Preparation of 2',2'-difluoro-5,6-dihydro-5-azadeoxycytidine (Compound VI). 3',5'-dibenzoyl-2',2'-difluoro-5-azadeoxycytidine (Compound V) (80 mg, 0.168 mmol), prepared as in Step A, was dissolved in 6 ml of anhydrous MeOH and 1 M NaOMe in MeOH (0.3 ml) was added. After 1 h at room temperature, the reaction mixture was quenched by addition of acetic acid (0.02 ml), evaporated and the deprotected product was isolated by RP HPLC on Gemini C18 5u (21.2×250 mm column) in 50 mM triethylammonium acetate (pH 7.5)-acetonitrile gradient. Appropriate fractions were pooled and evaporated to yield 49 mg (95% yield) of 2',2'-difluoro-5,6-dihydro-5-azadeoxycytidine (Compound VI).

$^1$H NMR in DMSO-d$_6$ for compound VI: 5.87 (dd, J$_1$=9.6 Hz, J$_2$=10.8 Hz, 1H, H1'), 4.51 and 4.29 (AB, 2H, CH$_2$), 3.98 (ddd, J$_1$=8.4 Hz, J$_2$=12.8 Hz, J$_3$=12.8 Hz, 1H, H3'), 3.67 (m, 1H, H5'), 3.58 (m, 1H, H4'), 3.52 (m, 1H, H5'). ESI MS: 267.0 [M+H]$^+$.

Scheme 2. Synthesis of 2',2'-difluoro-5,6-dihydro-5-azadeoxycytidine (Compound VI) (NUC014).

EXAMPLE 3

Preparation of 2'-Deoxy-2',2'-difluorozebularine (NUC019)

Preparation of 2'-deoxy-2',2'-difluorozebularine (Compound VIII) (NUC019) is shown in Scheme 3.

(1) The starting material 1-bromo-2-deoxy-2,2-difluoro-D-ribofuranosyl-3,5-dibenzoate (Compound I) was prepared as described in the Example 1.

(2) 2-Hydroxypyrimidine hydrochloride (0.57 g, 4.3 mmol) was suspended in hexamethyldisilazane (10 ml). The reaction mixture was heated at reflux for 1.5 h. The clear solution was decanted under argon, evaporated, coevaporated twice with dry xylene and vacuum dried.

(3) For glycosylation step, 1-bromo-2-deoxy-2,2-difluoro-D-ribofuranosyl-3,5-dibenzoate (Compound I) (1.20 g, 2.7 mmol), prepared as in Step (1), was dissolved in 20 ml of dichloroethane and transferred to the flask containing the silylated 2-hydroxypyrimidine. The reaction mixture was refluxed under argon for 16 hr, then dichloroethane was replaced with 10 mL of anisole, and the temperature was raised to 150° C. The reaction mixture was stirred at 150° C. for 18 hr, cooled to room temperature, and the product, 1-β-(2'-deoxy-2',2'-difluoro-D-ribofuranosyl)-pyrimidine-2-one (Compound VII), was isolated as a mixture of β- and α-isomers (1:6) by flash chromatography on silica gel in methanol/chloroform (3:97). Yield: 0.09 g or 7%.

(4) 1-β-(2'-Deoxy-2',2'-difluoro-D-ribofuranosyl)-pyrimidine-2-one (Compound VII), prepared as in Steps (1) to (3), (85 mg, 6:1 mixture of α and β isomers) was dissolved in 2 ml of anhydrous MeOH and 1 M NaOMe in MeOH (0.1 ml) was added. After 1 h at 4° C., the reaction mixture was evaporated and the deprotected isomers were isolated by RP HPLC on Gemini C18 5u (21.2×250 mm column) in 50 mM triethylammonium acetate (pH 7.5)-acetonitrile gradient. Immediately after separation fractions corresponding to β isomer were pooled and evaporated to yield 3.4 mg (7.4%) of 2'-deoxy-2',2'-difluorozebularine (Compound VIII).

$^1$H NMR in DMSO-$d_6$ for compound VIII β-isomer: 8.66 ppm (dd, $J_1$=4 Hz, $J_2$=2.4 Hz, 1H), 8.57 (dd, $J_1$=6.8 Hz, $J_2$=2.4 Hz, 1H), 6.62 (dd, $J_1$=6.8 Hz, $J_2$=4 Hz, 1H), 6.07 (t, J=7.2 Hz, 1H), 4.42-4.29 (m, 1H), 4.05-3.97 (m, 2H), 3.88-3.82 (m, 1H). ESI MS: 249 [M+H]$^+$.

Scheme 3. Synthesis of 2'-deoxy-2',2'-difluorozebularine (Compound VIII) (NUC019).

EXAMPLE 4

In Vitro Cytotoxicity of Pyrimidine Analogs

In this example, the in vitro cytotoxicity, as measured by $GI_{50}$ (50% of growth inhibition), of the following pyrimidine analogs was measured using assays known in the art: gemcitabine, 5-azadeoxycytidine, 5-azacytidine, 2',2'-difluoro-5-azadeoxycytidine (NUC013), 5,6-dihydro-5-azadeoxycytidine, and 2'-deoxy-2',2'-difluorozebularine (NUC019).

The in vitro cytotoxicity was measured in the following cell lines: NCI-H460 (ATCC #HTB-177) (non-small cell lung), HCT-116 (ATCC #CCL-247) (colorectal), HL-60 (ATCC #CCL-240) (leukemia), and MDA-MB-231 (ATCC #HTB-26) (breast). The calculated $GI_{50}$ values are shown in Table 4.

TABLE 4

Growth Inhibition ($GI_{50}$) Values (μM) for Selected Cell Lines.

| Compound | NCI-H460 | MDA-MB-231 | HCT-116 | HL-60 |
|---|---|---|---|---|
| gemcitabine | 0.02 | 0.72 | 0.01 | 0.03 |
| 5-azadeoxycytidine | 13.04 | >31.25 | >31.25 | 0.27 |
| 5-azacytidine | 0.43 | 1.64 | 0.62 | 0.44 |
| 2',2'-difluoro-5-azadeoxycytidine (NUC013) | 4.39 | >31.25 | 4.54 | 1.51 |
| 5,6-dihydro-5-azacytidine | 4.84 | >31.25 | 21.40 | 0.03 |
| 2'-deoxy-2',2'-difluorozebularine (NUC019) | 135.65 | 165.90 | 310.26 | — |

EXAMPLE 5

In Vitro DNA Methyltransferase Inhibition

The activity of DNA methyltransferase (DNMT) was measured in the cancer cell line HCT-116 (ATCC #CCL-247) (colorectal) and the percent inhibition of DNMT resulting from treatment of the cells with 5-azacytidine (5-aza-C) or 2',2'-difluoro-5-azadeoxycytidine (Compound IV) (NUC013) was calculated. The assay was performed using the EpiQuick DNA Methyltransferase Activity/Inhibition Assay Kit (Epigentek, Brooklyn, N.Y.). The HT-116 cells were incubated with 1 μM and 10 μM concentrations of each drug for a period of 24 hours. The percent inhibition of DNMT is shown in Table 5.

TABLE 5

Percent Inhibition of DNMT

| Experiment | 5-aza-C 1 μM | Compound IV (NUC013) 1 μM | 5-aza-C 10 μM | Compound IV (NUC013) 10 μM |
|---|---|---|---|---|
| 1 | N/A | N/A | 30.41 | 28.20 |
| 2 | 36.76 | 61.73 | 59.90 | N/A |
| 3 | 9.94 | 35.77 | 41.26 | 46.51 |
| 4 | 10.96 | 62.63 | 74.22 | 70.75 |

The results in Table 8 demonstrate that 2',2'-difluoro-5-azadeoxycytidine (NUC013) is an inhibitor of DNA methyltransferase.

While the preferred embodiment of the invention has been illustrated and described, it will be appreciated that various changes can be made therein without departing from the spirit and scope of the invention.

The embodiment of the invention in which an exclusive property or privilege is claimed are defined as follows:

1. A method for inhibiting DNA methyltransferase in a subject in need thereof, comprising administering a therapeutically effective amount of 2',2'-difluoro-5-aza-2'-deoxycytidine or a pharmaceutically acceptable salt thereof to the subject.

2. The method of claim 1, wherein the subject is a human.

3. A method for treating a cancer treatable by inhibiting DNA methyltransferase, comprising administering a therapeutically effective amount of 2',2'-difluoro-5-aza-2'-deoxycytidine or a pharmaceutically acceptable salt thereof to a subject in need thereof.

4. A method of treating a solid tumor carcinoma, consisting of administering a therapeutically effective amount of 2',2'-difluoro-5-aza-2'-deoxycytidine or pharmaceutically acceptable salt thereof in a pharmaceutically acceptable carrier to a subject in need thereof.

5. The method of claim 4, wherein the solid tumor carcinoma is selected from the group consisting of breast, non-small cell lung, colon, renal, ovarian, and colorectal carcinomas.

6. A method of treating a hematologic malignancy, consisting of administering a therapeutically effective amount of 2',2'-difluoro-5-aza-2'-deoxycytidine or pharmaceutically acceptable salt thereof in a pharmaceutically acceptable carrier to a subject in need thereof.

7. The method of claim 6, wherein the hematologic malignancy is a leukemia.

8. The method of claim 7, wherein the leukemia is resistant to decitabine (5-aza-2'-deoxycytidine).

9. 2',2'-Difluoro-5,6-dihydro-5-aza-2'-deoxycytidine, its anomers, or a pharmaceutically acceptable salt thereof.

10. A pharmaceutical composition, comprising a compound of claim 9 or a pharmaceutically acceptable salt thereof, and a pharmaceutically acceptable carrier.

11. A method of treating a solid tumor carcinoma, comprising administering a therapeutically effective amount of a compound of claim 9 or a pharmaceutically acceptable salt thereof to a subject in need thereof.

12. The method of claim 11, wherein the solid tumor carcinoma is selected from the group consisting of breast, non-small cell lung, and colon carcinomas.

13. The method of claim 11, wherein the subject is a human.

14. A method of treating a hematological malignancy, comprising administering a therapeutically effective amount of a compound of claim 9 or a pharmaceutically acceptable salt thereof to a subject in need thereof.

15. The method of claim 14, wherein the hematologic malignancy is a leukemia.

16. 2'-Deoxy-2',2'-difluorozebularine, its anomers, or a pharmaceutically acceptable salt thereof.

17. A pharmaceutical composition, comprising a compound of claim 16 or a pharmaceutically acceptable salt thereof, and a pharmaceutically acceptable carrier.

18. A method of treating a solid tumor carcinoma, comprising administering a therapeutically effective amount of a compound of claim 16 or a pharmaceutically acceptable salt thereof to a subject in need thereof.

19. The method of claim 18, wherein the solid tumor carcinoma is selected from the group consisting of breast, non-small cell lung, colon, and colorectal carcinomas.

20. The method of claim 18, wherein the subject is a human.

21. A method of treating a hematological malignancy, comprising administering a therapeutically effective amount of a compound of claim 16 or a pharmaceutically acceptable salt thereof to a subject in need thereof.

22. The method of claim 21, wherein the hematologic malignancy is a leukemia.

* * * * *